US00PP18701P2

(12) United States Plant Patent
Bradford

(10) Patent No.: US PP18,701 P2
(45) Date of Patent: Apr. 1, 2008

(54) NECTARINE TREE NAMED 'CANDYSWEET V'

(50) Latin Name: *Prunus persica*
Varietal Denomination: Candysweet

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/637,895

(22) Filed: Dec. 13, 2006

(51) Int. Cl.
*A01H 5/00* (2006.01)

(52) U.S. Cl. ..... Plt./190
(58) Field of Classification Search ..... Plt./190
See application file for complete search history.

(56) References Cited

U.S. PATENT DOCUMENTS

PP7,507 P 4/1991 Bradford et al.
PP9,963 P 7/1997 Bradford et al.

*Primary Examiner*—Kent Bell

(57) ABSTRACT

The present invention relates to a new and distinct variety of nectarine tree, *Prunus persica,* broadly characterized by a large size, vigorous, hardy, self-fertile, productive and regular bearing tree. The fruit matures under the ecological conditions described in mid June, with first picking on Jun. 18, 2006. The fruit is uniformly medium in size, sub-acidic and very sweet in flavor, globose in shape, clingstone in type, very firm in texture, yellow in flesh color, and almost full red in skin color.

1 Drawing Sheet

Botanical classification: *Prunus persica.*
Variety denomination: 'Candysweet V'.

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of nectarine tree, which has been denominated varietally as 'Candysweet V'. The present variety was hybridized by me in 2001, grown as a seedling on its own root in my greenhouse, and transplanted to a cultivated area of my experimental orchard near Le Grand, Calif., in Merced County (San Joaquin Valley).

The variety was developed as a first generation cross using 'Spring Bright' (U.S. Plant Pat. No. 7,507) nectarine as the selected seed parent and 'Ruby Sweet' (U.S. Plant Pat. No. 9,963) nectarine as the selected pollen parent. A single tree from the stated cross was selected as the claimed variety. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its selected seed parent, 'Spring Bright' nectarine, by producing fruit that is nearly globose in shape, yellow in flesh color, and full red in skin color, but is distinguished therefrom by producing nectarines that are sub-acidic instead of acidic in flavor and that mature about one week earlier.

The present variety is similar to its selected pollen parent, 'Ruby Sweet' nectarine, by producing nectarines that are nearly globose in shape, firm in texture, sub-acidic in flavor, and yellow in flesh color, but is distinguished therefrom by having a sweet instead of bitter kernel and by producing fruit that is sweeter in flavor and that matures about two weeks earlier.

SUMMARY OF VARIETY

In summary, the present variety is characterized by a large size, vigorous, hardy, self-fertile, productive and regular bearing tree. The fruit matures under the ecological conditions described in mid June, with first picking on Jun. 18, 2006. The fruit is uniformly medium in size, sub-acidic and very sweet in flavor, globose in shape, clingstone in type, very firm in texture, yellow in flesh color, and almost full red in skin color.

DRAWING

The accompanying photograph consists of four whole fruits positioned to display the characteristics of the skin color and form, one fruit divided around the suture plane to reveal the flesh and stone, two insets to reveal buds and a blossom, various leaves, and a typical tip shoot.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jun. 22, 2006, on the original tree during its fifth growing season. All major color code designations are by reference to the Inter-Society Color Council, National Bureau of Standards. Common color names are also used occasionally.

Tree

Size: Large, reaching and maintaining a height of 11' [3.35 m.] and a spread of 9' [2.74 m.] after five growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.
Growth: Spreading and dense.
Form: Vase formed.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Productive, thinning necessary.
Fertility: Self-fertile.
Bearing: Regular bearer with no alternate bearing yet observed.
Approximate chilling requirement: 575 hours.
Trunk:
*Size.*—Medium, reaching a maximum diameter of 3¾" [95 mm.] after the fifth growing season.
*Texture.*—Shaggy.
*Bark color.*—A Grayish brown [61. gy.Br] and Deep brown [56. deep Br] variegation.
*Lenticels.*—Approximate Number Per Square Inch: 12. Color: Dark orange yellow [72. d.OY]. Typical Size: ⅛" [3.2 mm.] to 7/16" [11.1 mm.]. Shape: Eye-shaped to elongated.
Branches:
*Size.*—Diameter of limb is 2⅝" [67 mm.], measured 12" above the crotch, 1½" [38 mm.] measured 12" above the first fork.
*Texture.*—Smooth on first and second year wood, increasing roughness with age.
*Color.*—1st Year Wood Topside: Grayish red [19. gy.R]. 1st Year Wood Underside: Brilliant yellow green [116. brill.YG]. Older Wood: Moderate olive brown [95. m.OlBr].
*Lenticels.*—Number Per Square Inch: More than 50 on second year wood. Color: Light yellowish brown [76. l.yBr]. Typical size: 1/64" [0.4 mm.] to 3/32" [2.4 mm.] on second year wood. Shape: Elongated.
Leaves:
*Size.*—Medium. Average Length: 5½" [140 mm.]. Average width: 1⅞" [48 mm.].
*Arrangement.*—Alternate.
*Thickness.*—Medium.
*Form.*—Elliptical.
*Apex.*—Acuminate.
*Base.*—Acute, with a base angle of 70 to 80 degrees.
*Surface.*—Smooth.
*Color.*—Dorsal Surface: Moderate olive green [125. m.OlG]. Ventral Surface: Moderate yellow green [120. m.YG].
*Margin.*—Finely serrate.
*Venation.*—Pinnately net veined.
*Vein color.*—Light yellow green [119. l.YG].
*Petiole.*—Average Length: ⅜" [9.5 mm.]. Average Thickness: 1/16" [1.6 mm.]. Color: Strong yellow green [117. s.YG].
*Stipules.*—Number: Usually 2 per leaf, up to 6 per growing tip. Average Length: ¼" [6.4 mm.]. Color: Very yellow green [115. v.YG] becoming Moderate reddish brown [43. m.rBr] with maturity.
*Glands.*—Number: 2 to 4 per leaf. Position: Alternately positioned on petiole and base of blade. Size: Medium. Form: Reniform. Color: Very yellow green [115. v.YG] becoming Strong yellowish brown [74. s.yBr] with age.
*Leaf buds.*—Pointed, medium in size.
Flower buds:
*Hardiness.*—Hardy, with respect to central California winters.
*Diameter.*—Typically ⅜" [9.5 mm.] 1 week before bloom.
*Length.*—Typically 11/16" [17.5 mm.] 1 week before bloom.
*Form.*—Not appressed.
*Surface.*—Pubescent.
*Color.*—Light purplish pink [249. l.pPk].
Flowers: Perfect, complete, perigynous, usually a single pistil, typically thirty or more stamens, five sepal and petal locations alternately positioned.
*Type.*—Showy, very large.
*Average flower diameter.*—2 1/16" [52.4 mm.].
*Number of petals.*—Usually five, extra petal fragments and double blossoms rare.
*Petal shape.*—Circular to oval.
*Petal margin.*—Somewhat wavy.
*Average petal diameter.*—13/16" [20.6 mm.].
*Average petal length.*—⅞" [22.2 mm.].
*Petal apex.*—Rounded.
*Petal base.*—Rounded to somewhat truncate.
*Petal color.*—Pale pink [7. p.Pk] toward the apex, Light pink [4. l.Pk] to Moderate purplish pink [250. m.pPk] toward the base.
*Anther color.*—Dark reddish orange [38. d.rO] over a Light yellow [86. l.Y] centers at bloom onset.
*Stigma color.*—Light greenish yellow [101. l.gY].
*Sepal color.*—Dark purplish red [259. d.pR].
*Sepal length.*—¼" [6.4 mm.].
*Sepal width.*—3/16" [4.8 mm.].
*Average pistil length.*—13/16" [20.6 mm.].
*Average stamen length.*—⅝" [15.9 mm.].
*Fragrance.*—Moderate.
*Blooming period.*—Medium, two days after 'Spring Bright' (U.S. Plant Pat. No. 7,507) nectarine.
*Onset of bloom.*—One percent on Feb. 27, 2006.
*Date of full bloom.*—Mar. 9, 2006.
*Duration of bloom.*—One to two weeks, dependent on ambient temperature.
*Number per cluster.*—1 to 3 with single flowers most common.

FRUIT

Maturity when described: Firm ripe, Jun. 22, 2006.
Date of first picking: Jun. 18, 2006.
Date of last picking: Jun. 28, 2006.
Size: Uniform, medium.
*Average diameter axially.*—2 11/16" [68 mm.].
*Average diameter across suture plane.*—2 13/16" [71 mm.].
*Average diameter across cheek plane.*—2 13/16" [71 mm.].
*Typical weight.*—7.0 ounces [198 grams].
Form: Uniform, globose.
*Longitudinal section form.*—Elliptical to slightly obovate.
*Axial view.*—Round.
Suture: A shallow groove extending from the base, along the side, and just past the pistil point, sharper in the stem cavity and toward the base.

Ventral surface: Rounded, lipped stronger toward the apex.
Lips: Slightly unequal.
Cavity: Flaring, circular to slightly elongated in the suture plane, suture showing on one side, Brilliant orange yellow [67. Brill.OY] stem markings typical.
*Depth.*—3/8" [9.5 mm.].
*Breadth.*—1 1/8" [28.6 mm.].
Base: Truncate, but slightly cordate if viewed parallel to the suture.
Apex: Rounded, but slightly cordate if viewed parallel to the suture.
Pistil point: Mostly apical, negligible in length, depressed within the suture.
Stem: Medium.
*Average length.*—3/8" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Non-astringent.
*Tendency to crack.*—Slight.
*Color.*—Very dark red [17. v.d.R] over a Very deep red [14. v.deep R] background with heavy Light orange yellow [70. l.OY] freckling toward the apex.
Flesh:
*Color.*—Brilliant yellow [83. brill.Y] from the stone to the skin, but will acquire a slight amount of Very red [11. v.R] flecking next to the skin with maturity.
*Surface of pit cavity.*—Light yellow [86. l.Y] broken fibers when twisted from stone.
*Amygdalin.*—Scarce.
*Juice.*—Moderate, rich.
*Texture.*—Firm, crisp, melting.
*Fibers.*—Abundant, fine.
*Ripens.*—Earlier at the apex.
*Flavor.*—Sub-acid and very sweet, typically 18 to 20 brix.
*Aroma.*—Slight.
*Eating quality.*—Excellent.

STONE

Type: Clingstone.
Form: Oval.
Hilum: Narrow.
Base: Straight.
Apex: Acute with an average angle of 65 to 85.
Sides: Equal.
Surface: Regularly furrowed toward the apex, pitted toward the base.
Ridges: Jagged.
External color: Light yellowish brown [76. l.yBr].
Pit wall color when cracked: Light orange yellow [70. l.OY].
Cavity surface color: Pale orange yellow [73. p.OY].
Average pit wall thickness: 1/4" [6.4 mm.].
Average width: 1 1/16" [27.0 mm.].
Average length: 1 7/16" [36.5 mm.].
Average breadth: 5/8" [15.9 mm.].
Tendency to split: Moderate.
Kernel:
*Form.*—Oval.
*Skin color.*—Pale yellow [89. p.Y] when first removed.
*Pellicle color.*—Moderate yellow [87. m.Y].
*Vein color.*—Light yellow [86. l.Y].
*Taste.*—Sweet.
*Viable.*—Yes.
*Average width.*—7/16" [11.1 mm.].
*Average length.*—11/16" [17.5 mm.].
*Amygdalin.*—Slight.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to its selected pollen parent, 'Ruby Sweet' (U.S. Plant Pat. No. 9,963) nectarine, by producing nectarines that are nearly globose in shape, firm in texture, sub-acidic in flavor, and yellow in flesh color, but is distinguished therefrom by having a sweet instead of bitter kernel and by producing fruit that is sweeter in flavor and that mature about two weeks earlier.

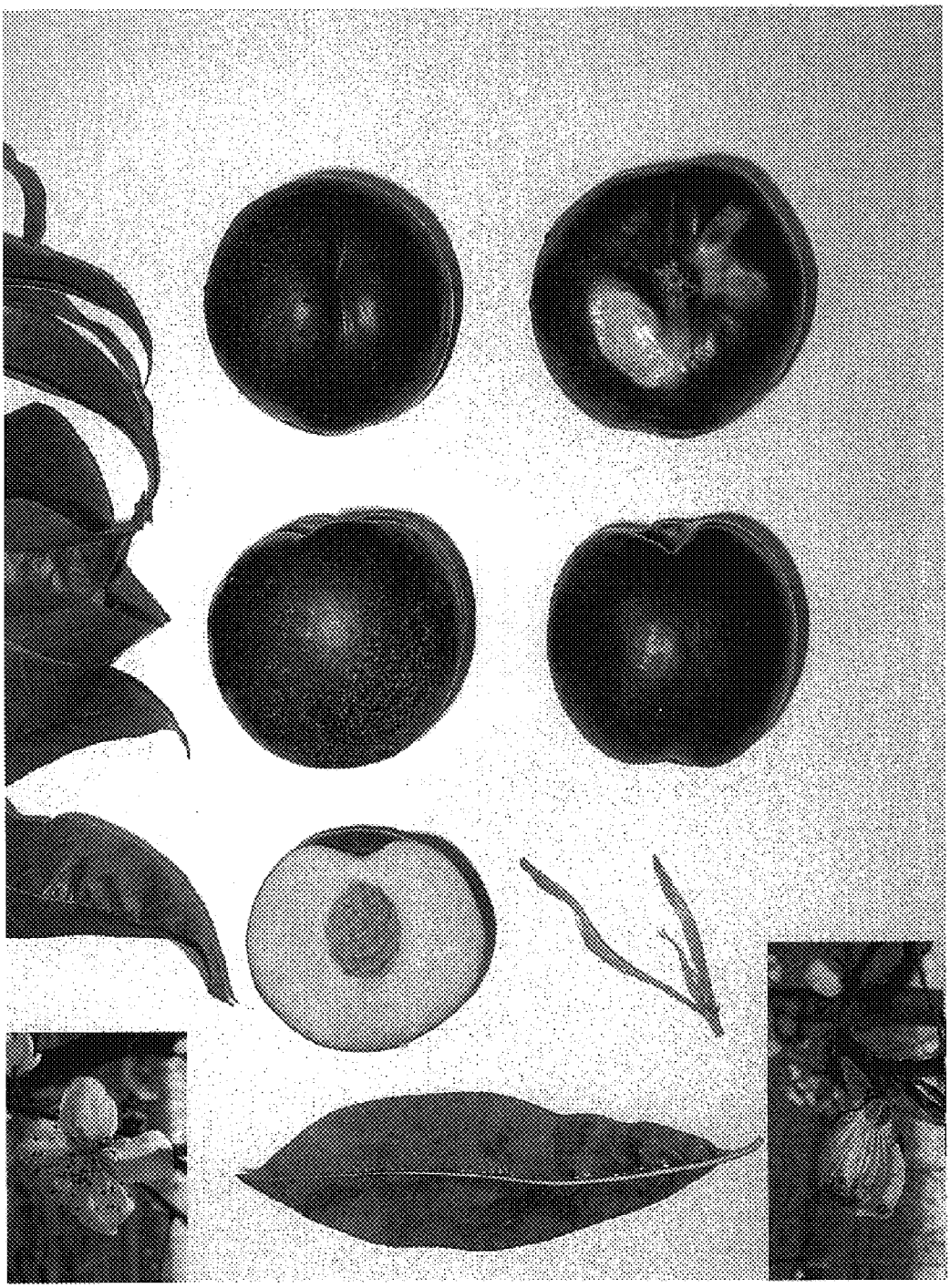

* * * * *